US006177063B1

(12) United States Patent
Hutchins

(10) Patent No.: US 6,177,063 B1
(45) Date of Patent: *Jan. 23, 2001

(54) ANHYDROUS AEROSOL HAIRSPRAY COMPOSITIONS CONTAINING SILCONE GRAFTED COPOLYMERS

(75) Inventor: Thomas Allen Hutchins, Cincinnati, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/067,637

(22) Filed: Apr. 28, 1998

(51) Int. Cl.[7] ............................... A61K 9/00; A61K 7/11; A61K 31/695; A01N 55/00

(52) U.S. Cl. ...................... 424/47; 424/70.11; 424/70.12; 424/70.16; 424/DIG. 1; 424/DIG. 2; 514/63

(58) Field of Search ................................ 424/47, DIG. 1, 424/DIG. 2, 70.11, 70.12, 70.16; 514/63

(56) References Cited

U.S. PATENT DOCUMENTS

| 5,104,646 | 4/1992 | Bolich, Jr. et al. | 424/70.12 |
|---|---|---|---|
| 5,106,609 | 4/1992 | Bolich, Jr. et al. | 424/70.12 |
| 5,120,532 | 6/1992 | Wells et al. | 424/70.12 |
| 5,658,557 | 8/1997 | Bolich, Jr. et al. | 424/70.12 |
| 5,811,109 | * 9/1998 | Cooper et al. | 424/401 |

FOREIGN PATENT DOCUMENTS

| 93/03703 | 3/1993 | (WO) | A61K/7/11 |
|---|---|---|---|
| 95/00106 | 1/1995 | (WO) | A61K/7/08 |
| 95/00108 | 1/1995 | (WO) | A61K/7/11 |

* cited by examiner

Primary Examiner—Carlos A. Azpuru
(74) Attorney, Agent, or Firm—William J. Winter; Linda M. Sivki

(57) ABSTRACT

Disclosed are anhydrous aerosol hairspray compositions which comprise (a) from about 0.1% to about 10% by weight of a silicone-grafted polycarboxylic acid copolymer having a weight average molecular weight of from about 10,000 to about 300,000, wherein the silicone-grafted polycarboxylic acid copolymer has a vinyl polymeric backbone, and a polysiloxane macromer grafted to the backbone wherein the polysiloxane macromer has a weight average molecular weight of from about 500 to about 50,000; (b) a neutralizing system comprising a combination of an organic and inorganic base, wherein the organic base is at a level sufficient to neutralize from about 25% to about 80% of the acid groups on the silicone-grafted copolymer while the inorganic base is at a level sufficient to neutralize from about 0.5% to about 20% of the acid groups on the silicone-grafted copolymer; (c) from about 5% to about 50% by weight of a nonhydrocarbon propellant that is substantially free of hydrocarbon propellants; and (d) the balance comprising a carrier suitable for application to hair. The anhydrous aerosol hairspray compositions defined herein do not weep or foam from the hairspray container, provide effective style retention, hair conditioning benefits, and do not feel unduly sticky or tacky to the touch.

19 Claims, No Drawings

ANHYDROUS AEROSOL HAIRSPRAY COMPOSITIONS CONTAINING SILCONE GRAFTED COPOLYMERS

TECHNICAL FIELD

The present invention relates to anhydrous aerosol hairspray compositions which comprise silicone-grafted polycarboxylic acid copolymers, wherein the silicone-grafted copolymers are neutralized with a select combination of organic and inorganic neutralizing agents to provide for improved spray delivery performance.

BACKGROUND OF THE INVENTION

Hair styling compositions are well known and are commercially available in a variety of forms including mousses, gels, lotions, pumps, or hairsprays. Many of these compositions contain various hairstyling resins to provide temporary hair styling or "setting" benefits.

Hairstyling resins such as silicone-grafted copolymers are particularly useful in hair styling compositions such as hairsprays because these copolymers can provide good style retention benefits to the hair while also providing improved hair feel. In other words, the silicone-grafted copolymers can impart a tactile sense of softness and conditioning to the hair relative to conventional, non-silicone-containing resins without the tacky hair feel traditionally associated with non-silicone hair fixative polymers. The silicone grafted copolymers are typically used as neutralized copolymers because when these copolymers are used at least in partially neutralized form the copolymers provide for a hairspray composition that is easily removable by water and/or by shampooing and that has improved styling performance.

The use of neutralized silicone-grafted copolymers in hairspray compositions is well known, and typically the copolymers are neutralized with an inorganic or organic neutralizing base. Hairspray compositions which contain an inorganic neutralizing base generally comprise at least about 10% by weight of water to help solubilize the silicone-grafted copolymer. Moreover, aqueous hairspray compositions which contain neutralized silicone grafted copolymers can result in a polymeric film on the hair that feels sticky or tacky to the touch. Therefore, it is desirable to use neutralized silicone-grafted hair styling copolymers in compositions containing less than about 10% by weight of water, and preferably in compositions that are substantially anhydrous, in order to obtain the desired product performance.

One method of formulating hairsprays that contain less than about 10% by weight of water and which also contain neutralized silicone-grafted copolymers involves the use of a neutralizing system comprising a combination of an inorganic and organic base. These hairsprays have a clear appearance, deliver effective style retention, impart a hair conditioning effect, have a non-sticky hair feel, are easily brushed out, and at the same time have stable product and viscosity characteristics and remain fully stable under long term and stressed temperature storage. The neutralizing systems incorporated into these hairspray compositions typically comprise the inorganic and organic bases at selected ratios to achieve the desired copolymer neutralization and the corresponding improvement in hairstyle performance and product clarity. It has been found, however, that the use of neutralized silicone-grafted copolymers in anhydrous hairsprays can result in poor spray performance, especially when the hairspray is formulated as an anhydrous aerosol hairspray. These anhydrous aerosol hairsprays tend to weep and foam at the orifice of the hairspray container during application.

It has now been found that select neutralizing systems can be incorporated into anhydrous aerosol hairspray compositions that contain silicone-grafted polymers to improve the spray delivery performance of the composition. It has also been found that the spray delivery performance can be improved when the composition contains a nonhydrocarbon propellant that is substantially free of any hydrocarbon propellant, e.g. less than about 5% of hydrocarbon propellant by weight of the composition. The select neutralizing systems incorporated in these anhydrous aerosol hairsprays comprise a combination of an organic base at a level sufficient to neutralize from about 25% to about 80% of the acid groups on silicone-grafted copolymers, and an inorganic base at a level sufficient to neutralize from about 0.5% to about 20% of the acid groups on silicone-grafted copolymers.

In view of the foregoing, it is therefore an object of the present invention to provide an anhydrous aerosol hairspray composition which does not weep or foam at the aerosol container orifice during application, and which contains silicone-grafted copolymers and a select neutralizing system to neutralize the copolymers, and which also contains less than about 5% by weight of a hydrocarbon propellant. It is also an object of the present invention to provide an anhydrous aerosol hairspray composition which delivers effective style retention, impart a hair conditioning effect, and does not feel unduly sticky or tacky to the touch.

SUMMARY OF THE INVENTION

The present invention is directed to anhydrous aerosol hairspray compositions which comprise (a) from about 0.1% to about 10% by weight of a silicone-grafted polycarboxylic acid copolymer having a weight average molecular weight of from about 10,000 to about 300,000, wherein the silicone-grafted polycarboxylic acid copolymer has a vinyl polymeric backbone, and a polysiloxane macromer grafted to the backbone wherein the polysiloxane macromer has a weight average molecular weight of from about 500 to about 50,000; (b) a neutralizing system comprising a combination of an organic and inorganic base, wherein the organic base is at a level sufficient to neutralize from about 25% to about 80% of the acid groups on the silicone-grafted copolymer while the inorganic base is at a level sufficient to neutralize from about 0.5% to about 20% of the acid groups on the silicone-grafted copolymer; (c) from about 5% to about 50% by weight of a nonhydrocarbon propellant that is substantially free of hydrocarbon propellants; and (d) the balance comprising a carrier suitable for application to hair.

It has been found that anhydrous aerosol hairspray compositions which are substantially free of hydrocarbon propellants and which contain silicone-grafted copolymers neutralized with a neutralizing system containing a select combination of organic and inorganic base materials do not weep or foam at the aerosol container orifice during application. These compositions provide effective style retention, hair conditioning benefits, and do not feel unduly sticky or tacky to the touch.

DETAILED DESCRIPTION OF THE INVENTION

The anhydrous aerosol hairspray compositions of the present invention are non-weeping/non-foaming hairspray formulations which are substantially free of hydrocarbon propellants and which comprise a select neutralizing system suitable for neutralizing the silicone-grafted copolymers defined herein.

The term "anhydrous" as used herein means that the hairspray composition of the present invention, and the essential or optional components thereof, are substantially free of added or free water. From a formulation standpoint, this means that the hairspray compositions of the present invention contain less than about 5%, preferably less than about 3%, more preferably less than about 1%, most preferably zero percent, by weight of free or added water.

The term "ambient conditions" as used herein refers to surrounding conditions at about one atmosphere of pressure, at about 50% relative humidity, and at about 25° C.

The term "volatile" as used herein refers to materials which have a vapor pressure under ambient conditions of at least about 0.2 mm of Hg. Conversely, the term "non-volatile" as used herein refers to materials which have no measurable vapor pressure or which have a vapor pressure of less than about 0.2 mm of Hg under ambient conditions.

The anhydrous aerosol hairspray compositions of the present invention can comprise, consist of, or consist essentially of the essential elements and limitations of the invention described herein, as well as any of the additional or optional ingredients, components, or limitations described herein. All percentages, parts and ratios are by weight of the total composition, unless otherwise specified. All such weights as they pertain to listed ingredients are based on the active level and, therefore, do not include solvents or by-products that may be included in commercially available materials, unless otherwise specified.

Silicone-Grafted Styling Polymer

The anhydrous aerosol hairspray compositions of the present invention comprise silicone-grafted polycarboxylic acid styling copolymers. These polymers are known in the art, and are characterized by polysiloxane moieties covalently bonded to and pendant from a polymeric carbon-based backbone. The silicone-grafted styling copolymers provide a thin polymeric film on the hair from the hairspray composition which is removable with a shampoo.

The silicone-grafted styling copolymers can be made by any conventional or otherwise known polymerization techniques well known in the art. The concentration of the silicone-grafted copolymer in the hairspray composition should be sufficient to provide the desired hair styling performance, and generally ranges from about 0.1% to about 10%, preferably from about 2% to about 9%, more preferably from about 3% to about 7%, by weight of the composition.

The silicone-grafted polymers preferably have a weight average molecular weight of from about 10,000 to about 300,000, more preferably from about 30,000 to about 200,000, even more preferably from about 90,000 to about 165,000. The molecular weights and molecular weight distributions of polymers suitable for use in the anhydrous aerosol hairspray compositions of the present invention are determined by Size Exclusion Chromatography (SEC) techniques well known in the art. One such technique include separation of the molecules by the use of a crosslinked polystyrene-divinylbenzene column (MW range=100–107), a differential refractive index detector, and a differential viscometer. A universal calibration curve is prepared from monodispersed polystyrene standards of known molecular weight (MW) and molecular weight distribution (MWD). MW and MWD of the given polymer are determined based on concentration and viscosity responses relative to the calibration.

The backbone of the silicone-grafted copolymer is preferably a carbon chain derived from polymerization of ethylenically unsaturated monomers, but can also be cellulosic chains or other carbohydrate-derived polymeric chains to which polysiloxane moieties are pendant. The backbone can also include ether groups, ester groups, amide groups, urethane groups, and the like. The polysiloxane moieties can be substituted on the polymer or can be made by co-polymerization of polysiloxane-containing polymerizable monomers with non-polysiloxane-containing polymerizable monomers.

Preferred silicone-grafted copolymers comprise an organic backbone, preferably a carbon backbone derived from ethylenically unsaturated monomers, such as a vinyl polymeric backbone, and a polysiloxane macromer (especially preferred are polydialkylsiloxane, most preferably polydimethylsiloxane) grafted to the backbone. The silicone-grafted copolymer preferred for use herein are such that when formulated into the finished hairspray composition, and dried, the copolymer phase separates into a discontinuous phase which includes the polysiloxane macromer and a continuous phase which includes the backbone. It is believed that this phase separation property provides a specific orientation of the copolymer on the hair which results in the desired conditioning and styling benefits.

The vinyl polymeric backbone preferably has a glass transition temperature (Tg) or crystalline melting point (Tm) of at least about −20° C., preferably from about 20° C. to about 80° C., more preferably from about 20° C. to about 60° C. Styling polymers having these Tg or Tm values form styling films on hair that are not unduly sticky or tacky to the touch. As used herein, the abbreviation "Tg" refers to the glass transition temperature of the backbone of the polymer, and the abbreviation "Tm" refers to the crystalline melting point of the backbone, if such a transition exists for a given polymer. Preferably, both the Tg and the Tm, if any, are within the ranges recited hereinabove.

The polysiloxane macromer should have a weight average molecular weight of at least about 500, preferably from about 1,000 to about 50,000, more preferably from about 5,000 to about 40,000, most preferably about 10,000 to about 20,000.

The silicone grafted copolymers suitable for use in the anhydrous aerosol hairspray compositions of the present invention comprise "silicone-containing" (or "polysiloxane-containing") monomers, which form the silicone macromer pendant from the backbone, and non-silicone-containing monomers, which form the organic backbone of the polymer. The non-silicone-containing monomer units can be derived from hydrophilic and/or hydrophobic monomer units. Therefore, the silicone-grafted copolymers for use herein can comprise combinations of the hydrophilic and/or polysiloxane-containing monomer units described herein, with or without hydrophobic comonomers as described herein, provided that the resulting styling polymer has the requisite characteristics as described herein.

The silicone grafted styling copolymers generally comprise from about 0.1% to about 50%, preferably from about 0.5% to about 40%, more preferably from about 10% to about 25%, of polysiloxane-containing monomer units; from about 1% to about 99.9%, preferably from about 5% to about 80%, more preferably from about 15% to about 30% of hydrophilic monomers; and from 0% to about 99%, preferably from about 5% to about 92%, more preferably from about 50% to about 90% of hydrophobic monomers, by weight of the copolymer. The total level of hydrophobic and hydrophilic monomer units is preferably from about 50% to about 99.9%, more preferably from about 60% to about 99.5%, most preferably from about 75% to about 90%, by weight of the copolymer.

Preferred silicone grafted polymers comprise monomer units derived from at least one free radically polymerizable vinyl monomer or monomers and at least one hydrophilic monomer which is copolymerizable with the vinyl monomer wherein the hydrophilic monomer consists of hydrophilic carboxylate monomers and macromers having a Tg or Tm value of at least about −20° C. Other examples of suitable silicone-grafted polymers and their methods of preparation are described in U.S. Pat. No. 4,693,935, to Mazurek, issued Sep. 15, 1987; and U.S. Pat. No. 4,728,571, to Clemens et al. issued Mar. 1, 1988, which descriptions are incorporated herein by reference.

Nonlimiting examples of suitable hydrophilic monomers include, but are not limited to, acrylic acid, methacrylic acid, maleic acid, maleic anhydride, half esters of maleic anhydride, crotonic acid, and itaconic acid. These monomers are carbon based and contain acid functional groups which are neutralizable with the neutralizing system defined hereinafter. Preferred hydrophilic monomers include acrylic acid, methacrylic acid, and mixtures thereof.

Nonlimiting examples of hydrophobic monomers include, but are not limited to, acrylic or methacrylic acid esters of C1–C18 alcohols such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-1-propanol), cyclohexanol, neodecanol, 2-ethyl-1-butanol, 3-heptanol, benzyl alcohol, 2-octanol, 6-methyl-1-heptanol, 2-ethyl-1-hexanol, 3.5-dimethyl-1-hexanol, 3,5,5-tri-methyl-1-hexanol, 1-decanol, lodecanol, 1-hexadecanol, 1-octadecanol, and the like, the alcohols having from about 1–18 carbon atoms with the average number of carbon atoms being from about 4–12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene, vinyl toluene; and mixtures thereof Preferred hydrophobic monomers include n-butyl methacrylate, isobutyl methacrylate, 2-ethylhexyl methacrylate, methyl methacrylate, t-butylacrylate, t-butylmethacrylate, and mixtures thereof.

Suitable polymerizable polysiloxane-containing monomers include, but are not limited to, those monomers that conform to the formula:

  (I)

wherein X is an ethylenically unsaturated group, such as a vinyl group, which is copolymerizable with the non-silicone-containing monomers described herein; Y is a divalent linking group; R is a hydrogen, lower alkyl (e.g. $C_1$–$C_4$), aryl, alkylamino, tri ($C_1$–$C_4$ alkyl)siloxy or $C_1$–$C_4$ alkoxy; Z is a monovalent siloxane polymeric moiety; n is 0 or 1; and m is an integer from 1 to 3. These polymerizable polysiloxane-containing monomers have a weight average molecular weight as described above.

Preferably the polysiloxane-containing monomer is selected from one or more monomers that conform to the following formulas (II to VII):

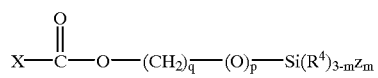 (II)

 (III)

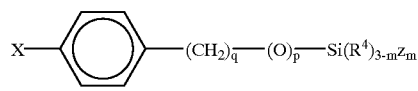 (IV)

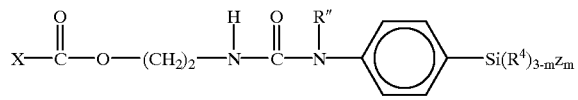 (V)

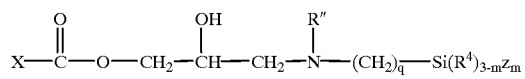 (VI)

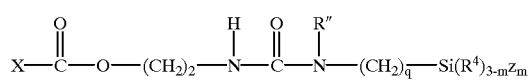 (VII)

wherein m is 1, 2 or 3 (preferably m=1); p is 0 or 1; q is an integer from 2 to 6; R″ is alkyl or hydrogen, X conforms to the formula:

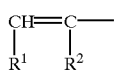

wherein $R^1$ is hydrogen or —COOH (preferably $R^1$ is hydrogen); $R^2$ is hydrogen, methyl or —$CH_2COOH$ (preferably $R^2$ is methyl); Z conforms to the formula:

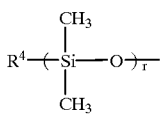

wherein $R^4$ is alkyl, alkoxy, alkylamino, aryl, or, hydroxyl (preferably $R^4$ is alkyl); and r is an integer of about 5 to about 700, preferably about 50 to about 500 (more preferably r is from about 150 to about 300). Of the above formulas, formula II is most preferred, particularly when p=0, and q=3.

Nonlimiting examples of some preferred silicone grafted copolymers for use in the anhydrous aerosol hairspray composition herein are listed below. Each listed polymer is followed by its monomer composition as part by weight of monomer used in the synthesis:

(i) acrylic acid/n-butylmethacrylate/polydimethylsiloxane ("PDMS") macromer—20,000 weight average molecular weight ("wt. avg. mw") macromer (10/70/20);
(ii) acrylic acid/isobutyl methacrylate/PDMS macromer—20,000 wt. avg. mw macromer (20/60/20);
(iii) acrylic acid/PDMS macromer—20,000 wt. avg. mw macromer (80/20);
(iv) t-butylacrylate(tBA)/acrylic acid(AA)/PDMS macromer—10,000 wt. avg. mw macromer (60/20/20);
(v) acrylic acid/isobutyl methacrylate/PDMS macromer—20,000 wt. avg. mw macromer (10/70/20);
(vi) acrylic acid/methyl methacrylate/PDMS macromer—20,000 wt. avg. mw macromer (40/40/20);
(vii) acrylic acid/isopropyl methacrylate/PDMS macromer—20,000 wt. avg. mw macromer (25/65/15);
(viii) acrylic acid/methoxyethyl methacrylate/PDMS macromer—20,000 wt. avg. mw macromer (60/25/15);
(ix) acrylic acid/PDMS macromer—20,000 wt. avg. mw macromer (80/20).

The silicone-grafted copolymers described above can be synthesized by free radical polymerization of silicone- or polysiloxane-containing monomers with non-silicone- or non-polysiloxane-containing monomers. The general principles of free radical polymerization methods are well understood. See, for example, Odian, "Principles of Polymerization", 2nd edition, John Wiley & Sons, 1981, pp. 179–318.

It may be desirable to purify the silicone-grafted copolymer by removing unreacted silicone-containing monomer and silicone macromer-grafted polymer with viscosities at 25° C. of about 10,000,000 centistokes and less. This can be done, for example, by hexane extraction. After drying the resin from its reaction solvent, hexane extraction of the reaction product can be performed by adding an excess of hexane to the reaction product and heating to near the Tg of the non-silicone portion of the polymer. The mixture is held at this temperature with stirring for about 30 minutes and cooled to room temperature. The hexane is removed by vacuum suction. Two more hexane extraction cycles are preferably conducted in the same manner as above. After the third cycle, residual hexane remaining with the product is removed by distillation and vacuum drying.

Low molecular weight polysiloxane-containing monomer and polymer is solubilized by supercritical carbon dioxide and transported away from the remaining polymer via a transfer line, which is maintained at identical temperature and pressure as the extraction vessel. The extracted materials are collected in an extraction vessel. Following extraction, the system is depressurised and dry, extracted polymer is recovered from the extraction vessel.

Neutralizing System

The anhydrous aerosol hairspray compositions of the present invention comprise a select combination of organic and inorganic bases to neutralize or partially neutralize the silicone-grafted styling copolymers described herein.

The anhydrous aerosol hairspray compositions of the present invention contain a total amount of a neutralizing system whereby from about 30% to about 99%, preferably from about 55% to about 95%, more preferably from about 80% to about 95% of the acidic monomers of the silicone-grafted copolymer are neutralized. The neutralizing system contains a combination of organic and inorganic base materials at a level sufficient to provide neutralization or partial neutralization of the carboxylic acid moieties of the silicone-grafted copolymers, wherein the organic base material is present at a level sufficient to neutralize from about 25% to about 80%, preferably from about 40% to about 80%, more preferably from about 50% to about 80% of the carboxylic acid moieties of the silicone-grafted copolymers; and wherein the inorganic base material is present at a level sufficient to neutralize from about 0.5% to about 20%, preferably from about 5% to about 20%, more preferably from about 10% to about 20% of the carboxylic acid moieties of the silicone-grafted copolymers.

Any conventional organic and inorganic base materials can be used in the hairspray compositions herein, provided that they are used in combination and in accordance with the requisite neutralization capacities described hereinbefore. Nonlimiting examples of suitable neutralizing materials include amines, ammonium hydroxide, hydroxides of alkali or alkaline earth metals, and mixtures thereof.

Specific nonlimiting examples of suitable inorganic base materials for use herein include ammonium hydroxide, and hydroxides of alkali and alkaline earth metals including potassium hydroxide, sodium hydroxide, and mixtures thereof. Preferred inorganic base materials include potassium hydroxide, sodium hydroxide, and mixtures thereof.

Nonlimiting examples of suitable organic base materials for use herein include amines, especially amino alcohols such as 2-amino-2-methyl-1,3-propanediol (AMPD), 2-amine-2-ethyl-1,3-propanediol (AEPD), 2-amino-2-methyl-1-propanol (AMP), 2-amino-1-butanol (AB), monethanolamine (MEA), diethanolamine (DEA), triethanolamine (TEA), monoisopropanolamine (MIPA), diisopropanolamine (DIPA), triisopropanolamine (TIPA), dimethyl steramine (DMS), dimethyl myristamine (DMM), dimethyl lauramine (DML), amino methyl propanol (AMP), and mixtures thereof. Preferred is amino methyl propanol.

The amount in grams of organic and inorganic base materials (Z) required to neutralize an acidic polymer can be deduced from calculations which take into account the acid value of the polymer (A); amount of polymer (W); mol wt of the base (B); mol wt of the acidic moiety (M) and the degree of neutralization required (N).

$$Z(g) = W \times A/100 \times 1/M \times B \times N\%$$

In the following example the amount of KOH required to neutralize 2.6 g of acrylic acid co-polymer (with an acid value of 20) to a level of 60% neutralization is calculated.

$Z(g) = 2.6 \times 20/100 \times 1/72 \times 56 \times 0.60$ $Z = 0.24$ g

Note, the acid value can be experimentally determined by titrating a specific amount of the polymer with base or theoretically by considering the original acidic content of the copolymer e.g. a polymer with 20% of acid monomer has an acid value of 20.

Liquid Carrier

The anhydrous aerosol hairspray compositions of the present invention comprise a suitable liquid carrier, preferably a liquid carrier at concentrations ranging from about 40% to about 99.8%, preferably from about 50% to about 95%, more preferably from about 55% to about 80%, by weight of the composition. The liquid carrier for use herein can comprise any known or otherwise effective liquid carrier for use in aerosol formulations intended for topical application to human hair or skin, e.g. liquid carriers for use in aerosol hairspray formulations. The liquid carrier can include solvents and other optional ingredients of the hairspray compositions of the present invention.

Suitable liquid carriers for use in the anhydrous aerosol hairspray composition of the present invention include organic solvents such as $C_1$–$C_6$ alkanols, carbitol, acetone, and mixtures thereof. Preferred liquid carriers are the $C_1$–$C_6$ alkanols. Nonlimiting examples of preferred $C_1$–$C_6$ alkanols include $C_2$–$C_4$ monohydric alcohols such as ethanol, isopropanol, and mixtures thereof.

Propellant

The anhydrous aerosol hairspray compositions of the present invention comprise a nonhydrocarbon propellant suitable for aerosol delivery of the hairspray composition to the desired application surface. To provide the improved spray performance benefits, the anhydrous aerosol hairspray composition must be substantially free of hydrocarbon propellants, e.g., contain less than about 5% by weight of such hydrocarbon propellants.

The anhydrous aerosol hairspray composition of the present invention contains less than about 5%, preferably less than about 3%, most preferably zero percent of hydrocarbon propellants by weight of the composition. It has been found that the spray performance of anhydrous aerosol hairspray compositions is improved by minimizing the concentration of the hydrocarbon propellants to less than about 5% by weight of the composition. In this context, the term "hydrocarbon propellants" as used herein refers to those liquifiable gases that contain only carbon and hydrocarbon atoms, most notably of which are propane, butane, and isobutane.

The total concentration of the nonhydrocarbon propellant in the anhydrous aerosol hairspray composition can include one or more nonhydrocarbon propellants, the total nonhydrocarbon propellant concentration typically ranging from about 5% to about 50%, preferably from about 15% to about 40%, more preferably from about 25% to about 40%, by weight of the composition. In this context, the term "nonhydrocarbon propellant" refers to all liquifiable gases suitable for use in topical application to human hair or skin, excluding the above-identified hydrocarbon propellants. Nonlimiting examples of suitable nonhydrocarbon propellants include nitrogen, carbon dioxide, nitrous oxide, atmospheric gas, 1,2-difluoroethane (Hydrofluorocarbon 152A) supplied as Dymel 152A by Dupont, dimethylether, and mixtures thereof. Preferred is dimethylether.

Water

The aerosol hairspray compositions of the present invention are anhydrous and therefore contain less than about 5%, preferably less than about 3%, more preferably less than about 1%, most preferably zero percent, of free or added water by weight of the composition.

Optional Components

The anhydrous aerosol hairspray compositions of the present invention may further comprise optional components known or otherwise effective for use in hair care or personal care products, provided that the optional components are physically and chemically compatible with the essential component described herein, or do not otherwise unduly impair product stability, aesthetics or performance. The concentration of such optional ingredients generally ranges from zero to about 25%, more typically from about 0.05% to about 25%, even more typically from about 0.1% to about 15%, by weight of the hairspray composition.

Nonlimiting examples of optional ingredients include preservatives, surfactants, conditioning or styling polymers other than and in addition to the silicone-grafted copolymers described herein, thickeners and viscosity modifiers, electrolytes, fatty alcohols, pH adjusting agents, perfume oils, perfume solubilizing agents, sequestering agents, emollients, lubricants and penetrants such as various lanolin compounds, protein hydrolysates and other protein derivatives, ethylene adducts and polyoxyethylene cholesterol, sunscreens, volatile and non-volatile silicone fluids, and isoparrafins.

The anhydrous aerosol hairspray compositions of the present invention can also be formulated to comprise a plasticizer at a concentration ranging from about 0.01% to about 25% by weight of the composition. The optional plasticizer is described in detail hereinafter.

Optional Plasticizer

The anhydrous aerosol hairspray compositions of the present invention may further comprise an optional nonvolatile plasticizer at concentrations effective to provide for improved hair style performance. Such concentrations generally range from about 0.01% to about 25%, preferably from about 0.1% to about 15%, more preferably from about 0.1% to about 5%, by weight of the composition. As used herein, the term "nonvolatile" in regard to plasticizers means that the plasticizer does not have a measurable vapor pressure under ambient conditions. The polymer-liquid carrier solution should not suffer from substantial plasticizer weight loss while the liquid carrier is evaporating, since this may excessively reduce plasticization of the polymer during use.

The optional plasticizers for use herein should generally have boiling points of from about 250° C. or higher. These materials are well known in the art and are described in *Kirk-Othmer Encyclopedia of Chemical Technology*, second edition, Volume 15, pp. 720–789 (John Wiley & Sons, Inc. New York, 1968) under the topic heading "Plasticizers"; in *The Technology of Plasticizers*, by J. Kern Sears and J. R. Darby (John Wiley & Sons, Inc., New York, 1982); and in the Appendix of Sears/Darby, Table A.9, pages 983–1063; which descriptions are incorporated herein by reference.

The optional plasticizers suitable for use in the anhydrous aerosol hairspray compositions of the present invention include both cyclic and acyclic nonvolatile materials. Non-limiting examples of suitable nonvolatile plasticizers include adipates, phthalates, isophthalates, azelates, stearates, citrates, trimellitates, silicone copolyols, iso $C_{14}$–$C_{22}$ alcohols, carbonates, sebacates, isobutyrates, oleates, phosphates, myristates, ricinoleates, pelargonates, valerates, camphor, glycols, and castor oil.

Preferred optional plasticizers for use herein include glycerin, diisobutyladipate (DIBA), glycols, and citrates. Preferred glycols include propylene glycol, dipropylene glycol and mixtures thereof. Preferred citrates include acetyl tri-n-butyl citrate, tri-n-butyl and acetyl tri-2-ethoxyhexyl citrate sold under the tradename Citroflex RTM supplied by Pfizer, and mixtures thereof

Method of Manufacture

The anhydrous aerosol hairspray compositions of the present invention may be prepared by any known or otherwise effective technique, suitable for providing an anhydrous aerosol hairspray composition provided that the neutralizing system is formulated to have and provide the requisite neutralization characteristics defined herein.

Methods for preparing the anhydrous aerosol hairspray compositions of the present invention include conventional formulation and mixing techniques. Suitable methods include adding the silicone-grafted copolymer to ethanol and mixing for several hours until the polymer is dissolved. The neutralizing system and optional plasticizer are then added, and the resulting solution is stirred. Any remaining ingredients such as water, and perfume can then be added. The composition is then packaged into a suitable container such as an aerosol dispenser.

The anhydrous aerosol hairspray composition of the present invention can be contained or dispensed in any known or otherwise effective aerosol container or delivery system. All such containers or delivery systems should be compatible with the essential and any selected optional ingredients of the hairspray composition of the present invention.

Alternatively, pressurized aerosol dispensers can be used where the propellant is separated from contact with the hairspray composition by use of specialized containers such as a two compartment can of the type sold under the tradename SEPRO from American National Can Corp.

Other suitable aerosol dispensers include those containing compressed air propellant which can be filled into the dispenser by means of a pump or equivalent device prior to use. Such dispensers are described in U.S. Pat. No. 4,077,441, to Olofsson, issued Mar. 7, 1978; and U.S. Pat. No. 4,850,577, to TerStege, issued Jul. 25, 1989. Compressed air aerosol containers suitable for use are also currently marketed by The Procter & Gamble Company under their tradename VIDAL SASSOON AIRSPRAY (RTM) hairsprays.

Method Of Use

The anhydrous aerosol hairspray compositions of the present invention are used in a conventional manner for providing hairstyle/hold benefits. An effective amount of the composition is sprayed onto dry or damp hair before and/or after the hair is styled. As used herein "effective amount" means an amount sufficient to provide the hair volume and style performance desired according to the length and texture of the hair.

The present invention is also directed to a method for controlling the weeping and foaming problem associated with the use of anhydrous aerosol hairspray compositions that are substantially free of hydrocarbon propellants, wherein the method of such control comprises the formulation of an anhydrous aerosol hairspray composition as defined herein which comprises the select combination of organic and inorganic base materials also defined herein.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. In the examples, all concentrations are listed as weight percent, unless otherwise specified. Each of the exemplified compositions are not unduly sticky or tacky to the touch, are easily removable with a shampoo, and do not weep or foam when packaged in an aerosol hairspray container.

Each of the exemplified compositions are in the form of an anhydrous aerosol hairspray concentrate which is suitable for application using an aerosol dispenser. The abbreviated terms used in the examples herein have the following designation:

| | |
|---|---|
| Hair Styling Copolymer | 60% t-butyl acrylate/20% acrylic acid/20% silicone PDMS. Weight average molecular weight (measured by SEC) of 150,000 |
| KOH | Potassium hydroxide solution, containing 45% potassium hydroxide and 55% water and minors |
| NaOH | Sodium hydroxide solution, containing 30% sodium hydroxide and 70% water and minors |
| AMP | 2-Amino-2-methyl-1-propanol |
| DMM | Dimethyl myristamine |
| DML | Dimethyl lauramine |
| Liquid carrier | Ethanol |

Aerosol Hairstyling Compositions

| | I | II | III | IV | V | VI |
|---|---|---|---|---|---|---|
| Hair Styling Copolymer | 7.70 | 4.61 | 10.0 | 7.70 | 6.15 | 3.07 |
| % copolymer neutralized with KOH | 15.0 | — | 5.00 | 5.00 | — | 20.0 |
| % copolymer neutralized with NaOH | — | 20.0 | — | — | 20.0 | — |
| % copolymer neutralized with AMP | 80.0 | 65.0 | — | 80.0 | — | 70.0 |
| % copolymer neutralized with DML | — | — | — | — | 75.0 | — |
| % copolymer neutralized with DMM | — | — | 70.0 | — | — | — |
| Balance[1] | to 100 percent with solvent | | | | | |

[1]The balance contains ethanol and optional ingredients such as isododecane, perfume and panthenol.

The anhydrous hairspray concentrate formulations are prepared by adding the silicone-grafted copolymer directly to the ethanol liquid carrier. A magnetic or air driven stirrer is used to mix the ingredients until the polymer is dissolved, typically about 1 to 2 hours. The neutralizing system (combination of organic and inorganic bases) is then added and mixed into the premix. Then the optional ingredients and water, as may be applicable, are mixed into the composition. The concentrates are packaged in conventional aerosol spray cans and are charged with a nonhydrocarbon liquifiable propellant such as dimethylether at a propellant-:concentrate weight ratio of 35:65.

What is claimed is:

1. An anhydrous aerosol hairspray composition comprising:
   (a) from about 0.1% to about 10% by weight of a silicone-grafted polycarboxylic acid copolymer having a weight average molecular weight of from about 10,000 to about 300,000, wherein the silicone-grafted polycarboxylic acid copolymer has a vinyl polymeric backbone, and a polysiloxane macromer grafted to the backbone wherein the polysiloxane macromer has a weight average molecular weight of from about 500 to about 50,000;
   (b) a neutralizing system comprising a combination of an organic and inorganic base, wherein the organic base is at a level sufficient to neutralize from about 25% to about 80% of the acid groups on the silicone-grafted copolymer while the inorganic base is at a level sufficient to neutralize from about 0.5% to about 20% of the acid groups on the silicone-grafted copolymer;
   (c) from about 5% to about 50% by weight of a nonhydrocarbon propellant that is substantially free of hydrocarbon propellants; and
   (d) the balance comprising a carrier suitable for application to hair;
   wherein said composition contains less than about 5%, by weight, of water; and
   wherein said composition contains less than about 5%, by weight, of hydrocarbon propellants.

2. The anhydrous composition of claim 1 wherein the composition comprises less than about 3% by weight of water.

3. The composition of claim 2 wherein the silicone-grafted copolymer has a weight average molecular weight of from about 30,000 to about 200,000.

4. The composition of claim 3 wherein the silicone-grafted copolymer comprises from about 50% to about 99.9% by weight of the vinyl polymeric backbone, and from about 0.1% to about 50% by weight of the polysiloxane macromer.

5. The composition of claim 4 wherein the vinyl polymeric backbone comprises from about 1% to about 99.9% of a hydrophilic carboxylate containing monomer and from 0% to about 99% of a hydrophobic monomer.

6. The composition of claim 5 wherein the hydrophilic carboxylate containing monomer is selected from the group consisting of acrylic acid, methacrylic acid, maleic acid, maleic anhydride, half esters of maleic anhydride, crotonic acid, itaconic acid, and mixtures thereof.

7. The composition of claim 5 wherein the hydrophobic monomer is selected from the group consisting of acrylic acid esters of C1–C18 alcohols, methacrylic acid esters of C1–C18 alcohols, styrene, polystyrene macromer, vinyl acetate, vinyl chloride, vinylidene chloride, vinyl propionate, alpha-methylstyrene, t-butylstyrene, butadiene, cyclohexadiene, ethylene; propylene, vinyl toluene, t, butylacrylate and mixtures thereof.

8. The composition of claim 4 wherein the polysiloxane macromer comprises polysiloxane-containing monomers which conform to the formula (1):

wherein X is a copolymerizable vinyl group; Y is a divalent linking group; R is a hydrogen, alkyl, aryl, alkylamino, trialkylsiloxy or alkoxy; Z is a monovalent siloxane polymeric moiety; n is 0 or 1; and m is an integer from 1 to 3.

9. The composition of claim 4 wherein the polysiloxane macromer comprises polysiloxane-containing monomers having the general formulas (II to VII):

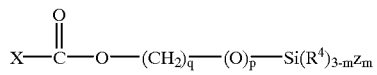

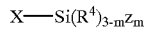

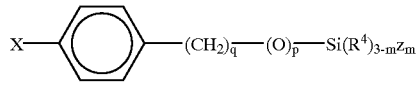

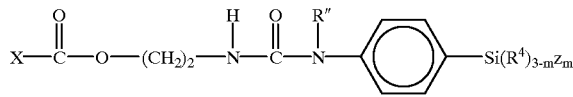

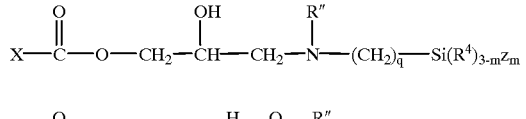

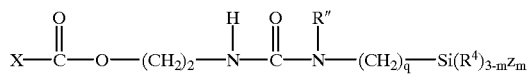

wherein m is 1, 2 or 3; p is 0 or 1; q is an integer from 2 to 6; R″ is alkyl or hydrogen, X conforms to the formula:

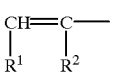

wherein $R^1$ is hydrogen or —COOH; $R^2$ is hydrogen, methyl or —$CH_2COOH$; Z conforms to the formula:

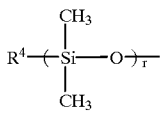

wherein $R^4$ is alkyl, alkoxy, alkylamino, aryl, or, hydroxyl; and r is an integer of about 5 to about 700.

10. The composition of claim 1 wherein the silicone-grafted copolymer is selected from the group consisting of:
 (i) acrylic acid/n-butylmethacrylate/polydimethylsiloxane macromer—20,000 wt. avg. mw macromer (10/70/20);
 (ii) acrylic acid/isobutyl methacrylate/polydimethylsiloxane macromer—20,000 wt. avg. mw macromer (20/60/20);
 (iii) acrylic acid/PDMS macromer—20,000 wt. avg. mw macromer (80/20);
 (iv) t-butylacrylate(tBA)/acrylic acid(AA)/polydimethylsiloxane macromer—10,000 wt. avg. mw macromer (60/20/20);
 (v) acrylic acid/isobutyl methacrylate/polydimethylsiloxane macromer—20,000 wt. avg. mw macromer (10/70/20);
 (vi) acrylic acid/methyl methacrylate/polydimethylsiloxane macromer—20,000 wt. avg. mw macromer (40/40/20);
 (vii) acrylic acid/isopropyl methacrylate/polydimethylsiloxane macromer—20,000 wt. avg. mw macromer (25/65/15);
 (viii) acrylic acid/methoxyethyl methacrylate/polydimethylsiloxane macromer—20,000 wt. avg. mw macromer (60/25/15);
 (ix) acrylic acid/polydimethylsiloxane macromer—20,000 wt. avg. mw macromer (80/20);
 (x) and mixtures thereof.

11. The composition of claim 1 wherein the neutralizing system comprises the organic base at a level sufficient to neutralize from about 40% to about 80% of the acid groups on the silicone-grafted copolymer, and the inorganic base at a level sufficient to neutralize from about 5% to about 20% of the acid groups on the silicone-grafted copolymer.

12. The composition of claim 11 wherein the organic base is selected from the group consisting of 2-amino-2-methyl-1,3-propanediol, 2-amine-2-ethyl-1,3-propanediol, 2-amino-2-methyl-1-propanol, 2-amino-1-butanol, monethanolamine, diethanolamine, triethanolamine, monoisopropanolamine, diisopropanolamine, triisopropanolamine, dimethyl steramine, dimethyl myristamine, dimethyl lauramine, amino methyl propanol, and mixtures thereof.

13. The composition of claim 11 wherein the inorganic base is selected from the group consisting of ammonium hydroxide, potassium hydroxide, sodium hydroxide, and mixtures thereof.

14. The composition of claim 11 wherein the acid groups of the silicone-grafted copolymer are neutralized to a total level of from about 30% to about 99%.

15. The composition of claim 1 wherein the composition comprises from about 15% to about 40% by weight of the nonhydrocarbon propellant.

16. The composition of claim 15 wherein the nonhydrocarbon propellant is selected from the group consisting of nitrogen, carbon dioxide, nitrous oxide, atmospheric gas, 1,2 difluoroethane, dimethylether, and mixtures thereof.

17. The composition of claim 1 wherein the carrier is selected from the group consisting of $C_1$–$C_6$ alkanols, carbitol, acetone, and mixtures thereof.

18. A method of controlling weeping and foaming of an anhydrous aerosol hairspray composition, said method comprising the steps of:
 (a) solubilizing a silicone-grafted polycarboxylic acid copolymer by combining the following ingredients:
  (i) from about 0.1% to about 10% by weight of a silicone-grafted polycarboxylic acid copolymer having a weight average molecular weight of from about 10,000 to about 300,000, wherein the silicone-grafted polycarboxylic acid copolymer has a vinyl polymeric backbone, and a polysiloxane macromer grafted to the backbone wherein the polysiloxane macromer has a weight average molecular weight of from about 500 to about 50,000; and
  (ii) from about 40% to about 99.8% by weight of a liquid carrier; and
 (b) mixing the solubilized silicone-grafted copolymer of step (a) with the following ingredients;
  (i) a neutralizing system comprising a combination of an organic and inorganic base, wherein the organic base is at a level sufficient to neutralize from about 25% to about 80% of the acid groups on the silicone-grafted copolymer while the inorganic base is at a level sufficient to neutralize from about 0.5% to about 20% of the acid groups on the silicone-grafted copolymer; and
  (ii) from about 5% to about 50% by weight of a nonhydrocarbon propellant that is substantially free of hydrocarbon propellants;
 wherein said anhydrous aerosol hairspray composition contains less than about 5%, by weight, of water; and
 wherein said anhydrous aerosol hairspray composition contains less than about 5%, by weight, of hydrocarbon propellants.

19. The method of claim 18 wherein the nonhydrocarbon propellant is selected from the group consisting of nitrogen, carbon dioxide, nitrous oxide, atmospheric gas, 1,2difluoroethane, dimethylether, and mixtures thereof.

* * * * *